United States Patent
Kosley, Jr. et al.

(10) Patent No.: US 6,323,196 B1
(45) Date of Patent: Nov. 27, 2001

(54) GALANTHAMINE DERIVATIVES AS ACETYLCHOLINESTERASE INHIBITORS

(75) Inventors: Raymond W. Kosley, Jr., Bridgewater; Larry Davis, Sergeantsville; Veronica Taberna, Union, all of NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 08/137,443

(22) Filed: Oct. 15, 1993

(51) Int. Cl.$^7$ .................. C07D 491/06; A61K 31/553; A61P 25/28
(52) U.S. Cl. .............................. 514/215; 540/581
(58) Field of Search .................. 540/581; 514/215

(56) References Cited

U.S. PATENT DOCUMENTS

| | | | |
|---|---|---|---|
| 4,663,318 | | 5/1987 | Davis .................. 514/215 |
| 5,231,093 | * | 7/1993 | Flanagan ............... 540/581 |
| 6,150,354 | * | 11/2000 | Davis .................. 540/581 |

FOREIGN PATENT DOCUMENTS

| | | |
|---|---|---|
| 0236684 | 11/1987 | (EP) . |
| 0535645 | 4/1993 | (EP) . |
| 2039892 | 11/1982 | (GB) . |
| 8800350 | 9/1989 | (NL) . |
| 88-8708 | * 11/1988 | (WO) . |
| 9220327 | 5/1992 | (WO) . |

OTHER PUBLICATIONS

Murray, et al, "Reversal By Tetrahydroaminoacridine of Scopolamine–Induced Memory and Performance Deficits in Rats" *Psychopharmacology 105*, pp. 134–136 (1991).
The Merck Index, 11$^{th}$ Edition, 1989, pp. 9003–9004, Tacrine.
The Merck Index, 10$^{th}$ Edition, No. 4210, p. 620.
Merck Manual, 16th Ed. (1992) p. 1398.*
Listor et al., Alz. Dis & Related Disorders 2, 219(1988).*
Costa, Soc. Neurosci Ab. 15, #46310 (1989).*
Robinson, Br. J. Pharm 98, 1127 (1989).*
Sarter, Psychopharm. 107, 144 (1992).*
Thompson, New E. J. Medicine 323, p. 445 (1990).*
Han. European J Med Chem 27, 673 (1992).*
Nordberg, in Alzheimer Disease & Related Disorders (1989) pp. 1169–1178.*
Derwent Patents Preview: CNS No. 1489 for ED 515 301 (1992).
Derwent Patents Preview: CNS No. 1490 for EP515302 (1992).

* cited by examiner

*Primary Examiner*—Mark L. Berch
(74) *Attorney, Agent, or Firm*—Balaram Gupta

(57) ABSTRACT

This application relates to compounds of the formula

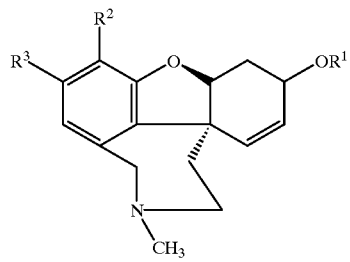

wherein $R^1$ is hydrogen, $(C_1-C_{12})$alkylcarbonyl, $(C_1-C_{12})$alkoxycarbonyl, mono$(C_1-C_{12})$alkylaminocarbonyl, or di$(C_1-C_{12})$alkylaminocarbonyl;

$R^2$ is mono$(C_1-C_{18})$alkylaminocarbonyloxy, di$(C_1-C_8)$alkylaminocarbonyloxy, or aryl$(C_1-C_4)$alkylaminocarbonyloxy;

$R^3$ is hydrogen or halo; or a pharmaceutically acceptable acid addition salt thereof, which compounds are useful for the treatment of memory dysfunction characterized by decreased cholinergic function, pharmaceutical compositions containing the compounds and methods for making and using the compounds.

21 Claims, No Drawings

GALANTHAMINE DERIVATIVES AS ACETYLCHOLINESTERASE INHIBITORS

This application relates to compounds of the formula

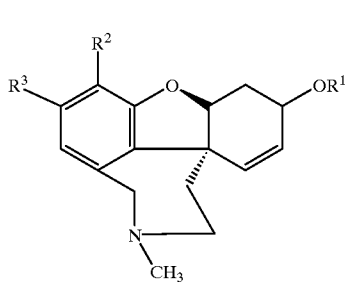

(I)

wherein
- $R^1$ is hydrogen, $(C_1-C_{12})$alkylcarbonyl, $(C_1-C_{12})$alkoxycarbonyl, mono$(C_1-C_{12})$alkylaminocarbonyl or di$(C_1-C_{12})$alkylaminocarbonyl;
- $R^2$ is $(C_1-C_{18})$monoalkylaminocarbonyloxy, $(C_1-C_{12})$ dialkylaminocarbonyloxy or aryl$(C_1-C_4)$ alkylaininocarbonyloxy);
- $R^3$ is hydrogen, halo or $(C_1-C_4)$alkyl; or a pharmaceutically acceptable addition salt thereof, which are useful for inhibiting acetylcholinesterase and alleviating various memory dysfunctions characterized by decreased cholinergic function such as Alzheimer's disease.

This invention also provides a pharmaceutical composition useful for inhibiting acetylcholinesterase and alleviating various memory dysfunctions characterized by decreased cholinergic function which comprises a compound of the invention in an amount sufficient to affect cholinergic function and a pharmaceutically acceptable carrier. This invention further provides a method for treating the effects of Alzheimer's disease which comprises treating a patient with a pharmaceutically effective amount of a compound of the invention.

Unless otherwise stated or indicated, the following definitions shall apply throughout the specification and appended claims.

The term "alkyl" shall mean a straight or branched alkyl group of the stated number of carbon atoms. Examples include, but are not limited to methyl, ethyl, n-propyl, iso-propyl, n-butyl, isobutyl, sec-butyl, t-butyl, and straight and branched chain pentyl, hexyl, heptyl, octyl, nonyl, decyl, undecyl, dodecyl and pentadecyl.

The term "halo" shall mean chloro, fluoro, bromo and iodo.

The term "aryl" shall mean phenyl having 0, 1, 2 or 3 substituents independently selected from the group of $(C_1-C_6)$alkyl, $(C_1-C_6)$alkoxy, $(C_1-C_6)$alkylcarbonyl, halo or trifluoromethyl.

In one embodiment of the invention are compounds of the formula

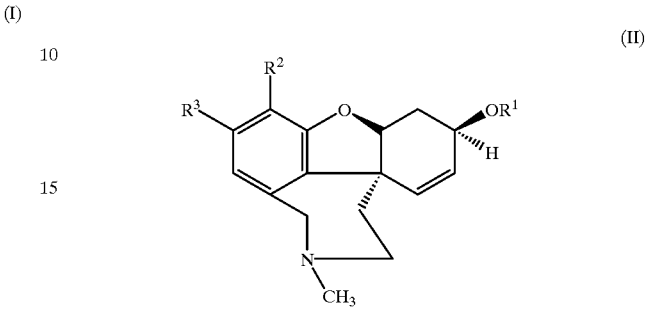

(II)

wherein
- $R^1$ is hydrogen, $(C_1-C_{12})$alkylcarbonyl, $(C_1-C_{12})$alkoxycarbonyl, mono$(C_1-C_{12})$alkylaminocarbonyl, or di$(C_1-C_{12})$alkylaminocarbonyl;
- $R^2$ is mono$(C_1-C_{18})$alkylaminocarbonyloxy, di$(C_1-C_8)$ alkylaminocarbonyloxy, or aryl$(C_1-C_4)$ alkylaminocarbonyloxy;
- $R^3$ is hydrogen or halo; and pharmaceutically acceptable addition salts.

In a preferred embodiment are compounds of Formula II wherein $R^1$ is hydrogen, $(C_1-C_{12})$alkylaminocarbonyl, phenyl$(C_1-C_4)$alkylaminocarbonyl, $(C_3-C_{12})$ Cycloalkylaminocarbonyl, $(C_1-C_{12})$alkylcarbonyl or $(C_1-C_{12})$alkoxycarbonyl; $R^2$ is $(C_1-C_{12})$ alkylaminocarbonyloxy or phenyl$(C_1-C_3)$ alkylaminocarbonyloxy; and $R^3$ is hydrogen or halogen.

More preferably $R^1$ is hydrogen, $(C_1-C_6)$alkylcarbonyl or $(C_1-C_6)$alkoxycarbonyl; $R^2$ is $(C-C_{10})$ alkylaminocarbonyloxy or phenyl$(C_1-C_2)$ alkylaminocarbonyloxy; and $R^3$ is hydrogen.

Most preferably $R^1$ is hydrogen, methylcarbonyl, ethylcarbonyl, isopropylcarbonyl, t-butylcarbonyl, n-heptylcarbonyl or t-butoxycarbonyl; $R^2$ is methylaminocarbonyloxy, isopropylaminocarbonyloxy, t-butylaminocarbonyloxy, n-pentylaminocarbonyloxy, n-hexylaminocarbonyloxy, n-heptylaminocarbonyloxy, n-octylaminocarbonyloxy or n-nonylaminocarbonyloxy; and $R^3$ is hydrogen.

The compounds of the invention are prepared from the appropriate derivative of galanthamine as described more fully below and shown in Scheme I.

SCHEME I

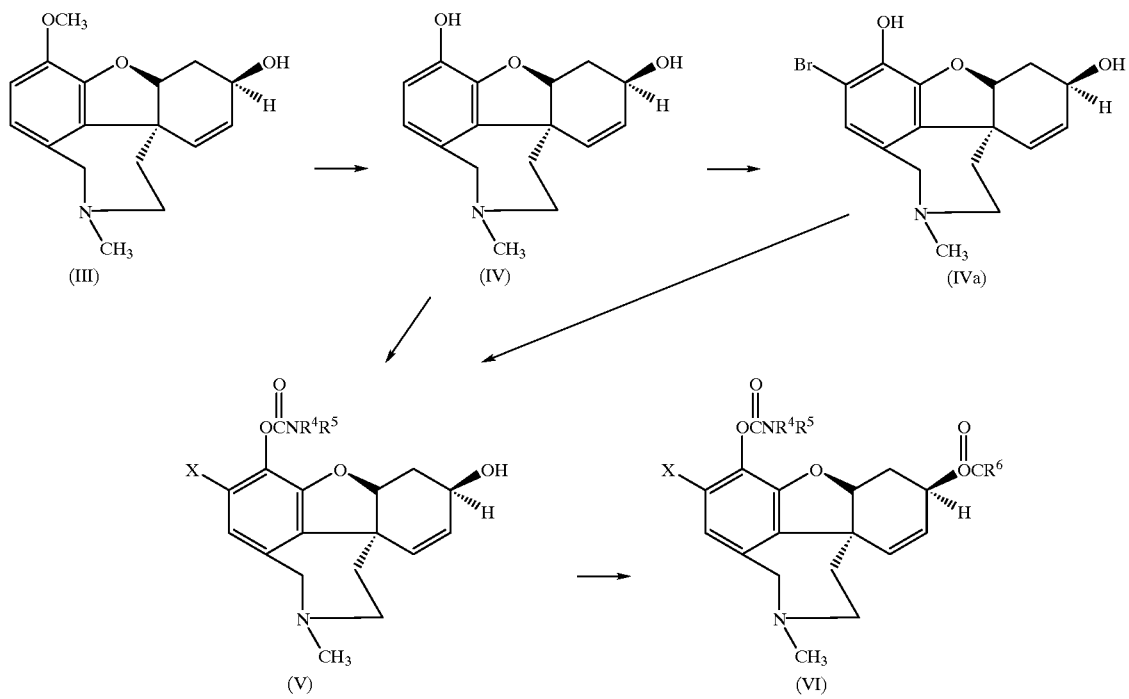

The intermediate 6-demethylgalanthamine of Formula IV, a known compound, was prepared in a novel process by treating the galanthamine of Formula III with an alkaline salt of ethanthiol such as, for example, with EtSLi, EtSNa or EtSK. The reaction is typically carried out in a polar nonprotic solvent such as dimethylformamide (DMF) or N-methylpyrrolidone or a protic solvent such as butanol or pentanol at from about 80° C. to about 135° C., preferably from about 90° C. to about 125° C.

The compound of Formula V wherein $R^4$ is hydrogen and $R^5$ is $(C_1-C_{12})$alkyl, or phenyl$(C_1-C_6)$alkyl is prepared by treating the compound of Formula IV with the appropriate isocyanato compound $R^5$NCO. The reaction is carried out in an aprotic solvent such as, for example, tetrahydrofuran in the presence of base such as, for example, potassium carbonate at from about −10° C. to about 30° C. for from about 0.5 hours to about 4 hours Alternatively and in the case where $R^4$ and $R^5$ are not hydrogen, the compound of Formula V is prepared by first reacting the compound of Formula IV with carbonyldumidazole and subsequently adding the appropriate $R^4R^5$NH compound. The reaction is typically carried out in a nonprotic organic solvent such as methylene chloride, chloroform or tetrahydrofuran (THF) at from about −10° C. to about 50° C., preferably from about 0° C. to about 30° C.

The compound of Formula VI can be prepared from the compound of Formula V. In the case where $R^6$ is alkylamino or arylamino, a solution of the appropriate isocyanate and the compound V in a nonprotic solvent such as tetrahydrofuran in a sealed tube at from about 55° C. to about 85° C. for from about 24 hours to about 120 hours, preferably from about 60° C. to about 70° C. for from about 60 hours to about 80 hours. Alternatively, where $NR^4R^5$ and $R^8$ are identical, the compounds are made from the compound of Formula IV using over two moles of the appropriate isocyanate in a sealed tube as described above.

In the case where $R^6$ is alkyl or aryl, the compound of Formula V is typically reacted with an appropriate carboxylic anhydride in the presence of a base such as 4-dimethylaminopyridine (DMAP) or pyrrolidinopyridine or carboxylic acid chloride in the presence of a base such as 1,8-diaza-bicyclo[5.4.0]undec-7-ene (DBU). The reactions are typically carried out in a non-protic solvent such as, for example, chloroform or dichloromethane at from about 0° C. to about 50° C., preferably at from about 15° C. to about 30° C.

In the case where $R^6$ is alkoxy or aryloxy, the compound of Formula V is typically reacted with the appropriate chloroformate in the presence of an amine such as triethylamine; or with the appropriate dicarbonate in the presence of an amine such as DMAP. The reactions are typically carried out in an inert organic solvent such as methylene chloride at from about −10° C. to about 50° C., preferably from about 0° C. to about 30° C.

In the case where X is Br, the compound of Formula IV is treated with bromine in the presence of an amine such as t-butylamine to obtain the brominated compound. The bromine is first added to the t-butylamine at from about −20° C. to about −30° C., then the reaction mixture is cooled to about −80° C. to about −70° C. and the galanthamine compound is added. The reaction is typically carried out in a nonpolar organic solvent such as for example toluene. Following addition of galanthamine the mixture is allowed to warm from about −70° C. to −80° C. to about room temperature for from about 6 hours to about 10 hours, preferably about 8 hours.

The compounds of Formula I of the present invention can be used for the treatment of various memory dysfunctions characterized by decreased cholinergic function, such as Alzheimer's disease. The compounds to of the present invention are advantageous because they are less toxic and/or more potent than the related compounds known in the art.

This utility is manifested by the ability of these compounds to inhibit the enzyme acetylcholinesterase and thereby increase acetylcholine levels in the brain.

The ability to inhibit acetylcholinesterase was determined by the photometric method of Eliman et al., Biochem. Pharmacol. 7,88 (1961). Results of acetylcholinesterase inhibition for some of the compounds of this invention are presented in Table I along with those for reference compounds.

TABLE I

Acetylcholinesterase Inhibition Assay

| Compound | $IC_{50}$ $\mu M$ CHE I |
|---|---|
| 6-O-Demethyl-6-O-(methylamino-carbonyl)galanthamine | 0.0020 |
| 6-O-Demethyl-6-O-methylaminocarbonyl-3-O-(2-propylcarbonyl)galanthamine hydrochioride | 0.047 |
| Tacrine | 0.32 |

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incandescent light drives it to the dark compartment, where arn electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compounds, resulting in a greater interval before re-entry into the dark compartment.

The test results are expressed as the percent of a group of animals in which the effect of scopolanine is blocked, as manifested by an increased interval between being placed in the test chamber and re-entering the dark compartment. Results of Dark Avoidance Assay for some of the compounds of this invention are presented in Table II along with a result for a reference compounds.

TABLE II

| Compound | SDDA Dose (mg/kg, s.c.) | Percent of Animals with Scopolamine Induced Memory Deficit Reversal |
|---|---|---|
| 6-O-Demethyl-6-O-(methylamino-carbonyl)galanthamine | 0.003 | 27 |
| Tacrine | 0.31 | 33 |

Effective quantities of the compounds of the invention may be administered to a patient by any of the various methods, for example, orally as in capsule or tablets, parenteraply in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 5% to about 70% of the weight of the unit. The amount of active compound in such compositions is such that a suitable dosage will be obtained. Preferred compositions and preparations according to the present invention are prepared so that an oral dosage unit form contains between 1.0–200 milligrams of active compound.

The tablets, pills, capsules, troches and the like may also contain the following ingredients: a binder such as microcrystalline cellulose, gum tragacanth or gelatin: an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above-type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants such as ascorbic acid or sodium bisulfite; chelating agents such as ethylenediaminetetraacetic acid; buffers such as acetates; citrates or phosphates and agents for the adjustment of tonicity such as sodium chloride or dextrose. The parenteral multiple dose vials may be of glasser plastic.

The following Table m and examples will further illustrate this invention but are not intended to limit it in any way. In Table III typical compounds of the instant invention are listed. Following Table III, representative illustrative preparations of compounds of the invention are described.

TABLE III

[Structure with R², R³, OR¹ substituents on galanthamine core, N-CH₃]

| EX. No. | R¹ | R² | R³ | m.p. °C |
|---|---|---|---|---|
| 1 | H | OH | H | 225–229* |
| 2 | H | OC(=O)NHCH₃ | H | 196–197 |
| 3 | H | OC(=O)NH(CH₂)₆CH₃ | H | 222–224ᵃ |
| 4 | H | OC(=O)NH(CH₂)₃CH₃ | H | 217–218d |
| 5 | H | OC(=O)NH(CH₂)₅CH₃ | H | 220–222ᵃ |
| 6 | C(=O)CH₃ | OC(=O)NHCH₃ | H | 178dᵃ |
| 7 | H | OC(=O)NH(CH₂)₇CH₃ | H | 210–212ᵃ |
| 8 | C(=O)NH(CH₂)₆CH₃ | OC(=O)NH(CH₂)₆CH₃ | H | 215–217ᵃ |
| 9 | H | OC(=O)NHC(CH₃)₃ | H | 230–232ᵃ |
| 10 | H | OC(=O)NHCH₂C₆H₅ | H | 210–212ᵇ |
| 11 | H | OC(=O)NH(CH₂)₈CH₃ | H | 205–208ᵃ |
| 12 | C(=O)NH(CH₂)₃CH₃ | OC(=O)NH(CH₂)₃CH₃ | H | 201–210ᵃ |
| 13 | C(=O)CH(CH₃)₂ | OC(=O)NHCH₃ | H | 135ᵃ |
| 14 | C(=O)CH(CH₃)₂ | OC(=O)NH(CH₂)₇CH₃ | H | 137–140ᵃ |
| 15 | C(=O)C(CH₃)₃ | OC(=O)NH(CH₂)₇CH₃ | H | 138–140 |
| 16 | H | OH | Br | 138–141 |
| 17 | H | OC(=O)NH(CH₂)₁₄CH₃ | H | 188–191dᵃ |
| 18 | H | OC(=O)N(CH₃)₂ | H | 270–272dᵃ |

*Lit. m.p. 220–222
ᵃisolated as HCl salt

EXAMPLE 1

6-O-Demethylgalanthamine

To a stirred solution of 20 ml of dry DMF at −40° under nitrogen was added 0.57 ml (0.48 g) of ethanethiol. The mixture was stirred for several minutes at −40° to −30° after which 2.84 ml of 2.5 M BuLi in hexanes was added slowly by syringe at −40° to −50°. The solution was then allowed to warm to room temperature over 15 minutes, heated to 50° under aspirator vacuum and again cooled to 30°. To the solution was added a solution of 0.57 g of galanthanine in 5.7 ml of dry DMF. The solution was stirred at 95–100° for 2 hours and subsequently at 100–105° for 3 hours, allowed to cool to room temperature and concentrated to an oil. The oil was dissolved in chloroform, shaken with NH₄Cl, made basic with aq NaHCO₃ and extracted four times with CHCl3. The pH of the aqueous layer was then adjusted to 9–10 with NH₄OH and again extracted four times with chloroform. The combined organic extracts were dried (Na2SO₄), filtered and concentrated to an oil. The oil was dissolved in degassed 5% methanol/chloroform and flash chromatographed on silica gel eluting with the same solvent system followed by 10% methanol/chloroform to provide a beige solid. The material was dissolved in acetone and allowed to crystallize overnight to provide 0.298 g of 6-O-demethylgalanthamine, m.p. 225–229°.

| ANALYSIS | | | |
|---|---|---|---|
| Calculated for C₁₆H₁₉NO₃ | 70.31% C | 7.01% H | 5.12% N |
| Found | 70.14% C | 7.29% H | 4.96% N |

EXAMPLE 2

6-O-Demethyl-6-O-(methylaminocarbonyl) galanthamine

To a solution of 6-O-demethylgalanthamine (0.5 g) in 30 ml of dry tetrahydrofuran, was added milled K₂CO₃ (0.3 g) followed by methyl isocyanate (0.1 ml).

After stirring at ambient temperature for twenty hours, the mixture was filtered, and the filtrate evaporated to a tan solid (0.5 g) which was recrystallized from methanol to give 0.3 g (53%) of a solid, m.p. 196–197° C. (dec.).

| ANALYSIS | | | |
|---|---|---|---|
| Calculated for C₁₈H₂₂N₂O₄ | 65.43% C | 6.71% H | 8.48% N |
| Found | 64.79% C | 6.81% H | 8.20% N |

EXAMPLE 3

6-O-Demethyl-6-O-(n-heptylaminocarbonyl) galanthamine Hydrochloride

To 0.614 g of 6-O-demethylgalanthamine and 0.62 g of milled potassium carbonate was added by syringe 10.5 ml of dry THF. The suspension was cooled in an ice/salt bath after which 0.4 ml of n-heptylisocyanate was added by syringe. The mixture was stirred for 20 minutes at ice bath temperature, allowed to warm to room temperature and stirred at room temperature for 15 minutes. The solution was diluted with dry dichloromethane, cooled in an ice bath to room temperature and poured onto a silica gel column packed with 3% dry methanol/dichloromethane. The column was eluted with this solvent system followed by 5% dry methanol/dichloromethane to provide 0.852 g of an oil. The material was dissolved in ether and the hydrochloride salt precipitated by addition of ethereal hydrogen chloride, filtered and dried to provide 0.711 g of white crystals. Recrystallization/trituration from isopropyl alcohol provided 0.536 g of 6-O-demethyl-6-O-(n-heptylaminocarbonyl)galanthamine hydrochloride, m.p. 222–224°.

| ANALYSIS | | | |
|---|---|---|---|
| Calculated for C₂₄H₃₄N₂O₄.HCl | 63.92% C | 7.82% H | 6.21% N |
| Found | 63.88% C | 8.19% H | 6.06% N |

EXAMPLE 4

6-O-Demethyl-6-O-(n-butylaminocarbonyl) galanthamine Hydrochloride

To a stirred suspension of 0.591 g of 6-O-demethylgalanthamine in 10 ml of THF was added 0.6 g of milled potassium carbonate. The suspension was cooled to 0° C. and 0.30 ml of n-butylisocyanate was added by syringe. The suspension was stirred for ½ hour at 0° and 45 minutes at room temperature. To the suspension, at room temperature was added an additional 0.30 ml of n-butylisocyanate after which the suspension was stirred for ½ hour at room temperature. The suspension was filtered onto a flash chromatography column packed with silica gel in 3% dry methanol/dichloromethane. Flash chromatography was carried out with 3% dry methanol/dichloromethane followed by 5% dry methanol/dichloromethane to provide an oil which was dissolved in ethyl acetate and the hydrochloride salt precipitated by addition of ethereal hydrogen chloride.

The material was isolated by filtration and dried to provide 0.611 g of material, m.p. 217–218° Cd.

| ANALYSIS | | | |
|---|---|---|---|
| Calculated for $C_{21}H_{28}N_2O_4$.HCl | 61.68% C | 7.15% H | 6.85% N |
| Found | 61.93% C | 7.09% H | 6.69% N |

EXAMPLE 5

6-O-Demethyl-6-O-(n-hexylaminocarbonyl) galanthamine Hydrochloride

To a mixture of 0.80 g of 6-O-demethylgalanthamine and 0.81 g of milled potassium carbonate was added 13.5 ml of THF via a syringe. The suspension was cooled to 0° C. and 0.54 ml of n-hexyl isocyanate was added by syringe. The suspension was filtered onto a flash chromatography column packed with silica gel and eluted with 3% dry methanol/dichloromethane followed by 5% dry methanol/dichloromethane. The pure, product-containing fractions were combined and concentrated to provide 0.93 g of a white solid which was dissolved in diethyl ether and the hydrochloride salt precipitated by addition of ethereal hydrogen chloride to provide 0.82 g of 6-O-demethyl-6-O-(n-hexylaminocarbonyl)galanthamine hydrochloride, m.p. 220–222° C.

| ANALYSIS | | | |
|---|---|---|---|
| Calculated for $C_{23}H_{32}N_2O_4$.HCl | 63.22% C | 7.61% H | 6.41% N |
| Found | 63.23% C | 7.72% H | 6.37% N |

EXAMPLE 6

3-O-Acetyl-6-O-demethyl-6-O-(methylaminocarbonyl)galanthamine Hydrate Hydrochloride To a suspension of 6-O-demethyl-6-O-(methylaminocarbonyl)galanthamine (0.4 g) in 25 ml of dichloromethane, was added 4-dimethylaminopyridine (0.3 g) and the mixture cooled to 0° C. To this was added acetic anhydride (0.2 ml) and the mixture stirred at 0° C. for one hour; then at ambient temperature for two hours.

The solution was eluted on a silica gel column with 10% methanol/dichloromethane, and the desired fractions combined, then evaporated to a white solid, 0.33 g, m.p. 72° C. This material was dissolved in methanol, the pH adjusted to 1 with ethereal-HCl, then diluted with ether. The resultant white precipitate was collected and dried to give 0.31 g, m.p. 178° C. (dec.).

| ANALYSIS | | | |
|---|---|---|---|
| Calculated for $C_{20}H_{24}N_2O_5$.HCl.2H$_2$O | 53.99% C | 6.57% H | 6.30% N |
| Found | 54.13% C | 6.60% H | 6.20% N |

EXAMPLE 7

6-O-Demethyl-6-O-(n-octylaminocarbonyl) galanthamine Hydrchloride

To a mixture of 0.791 g of 6-O-Demethylgalanthamine and 0.815 g of milled potassium carbonate was added 13.5 ml of THF via a syringe. The suspension was cooled to 0° C. and 0.65 ml of n-octyl isocyanate was added by syringe. The suspension was filtered onto a flash chromatography column, packed with silica gel, and eluted with 3% dry methanol/dichloromethane followed by 5% dry methanol/dichloromethane to provide 1.06 g of a white solid which was dissolved in diethyl ether, and the hydrochloride salt was precipitated by addition of ethereal hydrogen chloride to provide 0.91 g of a white solid. Trituration/recrystallization from isopropyl alcohol yielded material of m.p. 210°–212° C.

| ANALYSIS | | | |
|---|---|---|---|
| Calculated for $C_{25}H_{36}N_2O_4$.HCl | 64.57% C | 8.02% H | 6.02% N |
| Found | 64.54% C | 7.96% H | 5.88% N |

EXAMPLE 8

6-O-Demethyl-3-O,6-O-bis(n-heptylaminocarbonyl) galanthamine Hydrochloride

To a suspension of 0.8 g of 6-O-demethylgalanthamine in 14 ml of dry THF was added 1.7 ml of n-heptylisocyanate. The mixture was stirred at 72° C. in a sealed tube for 72 hours and the solution concentrated to an oil. The oil was dissolved in 5% methanol/chloroform and flash chromatographed on silica gel, eluting with the same solvent system. Approximately one half of the primary product was contained in one fraction which was contaminated by a small amount (2–5%) of the lower eluting monocarbamate. This fraction was concentrated to an oil and again flash chromatographed on silica gel, eluting with 5% methanol/chloroform. The pure product-containing fractions were combined and concentrated to an oil which was dissolved in ether and the hydrochloride salt precipitated by addition of ethereal HCl. The material was dried for 2 hours at 80° to provide 0.32 g of 6-O-demethyl-3-O,6-O-bis(n-heptylaminocarbonyl)galanthamine hydrochloride, m.p. 215–217.

| ANALYSIS | | | |
|---|---|---|---|
| Calculated for $C_{32}H_{49}N_3O_5$.HCl | 64.90% C | 8.51% H | 7.10% N |
| Found | 64.64% C | 8.59% H | 6.98% N |

EXAMPLE 9

6-O-Demethyl-6-O-(t-butylaminocarbonyl) galanthamine Hydrochloride

To a mixture of 1.01 g of 6-O-demethylgalanthamine and 1.03 g of milled potassium carbonate was added 16.9 ml of THF via a syringe. The suspension was cooled to 0° C. and 0.52 ml of t-butyl isocyanate was added by syringe. The suspension was stirred for ½ hour at 0° C. to 5° C. and at room temperature overnight. The suspension was dissolved in methanol and filtered onto a flash chromatography column, packed with silica gel, after which it was eluted with 3% dry methanol:chloroform followed by 5% dry methanol:chloroform. The product-containing fractions were combined and concentrated to provide 0.81 g of a white, amorphous solid. The solid was dissolved in chloroform, diluted with ethyl ether, and the hydrochloride salt was precipitated by addition of ethereal hydrogen chloride to provide 0.62 g of 6-O-demethyl-6-O-(t-butylaminocarbonyl)galanthamine hydrochloride. Trituration/recrystallization using ethanol provided yielded the desired product, m.p. 230–232° C.

| ANALYSIS | | | |
|---|---|---|---|
| Calculated for $C_{21}H_{28}N_2O_4 \cdot HCl$ | 61.68% C | 7.15% H | 6.85% N |
| Found | 61.46% C | 7.36% H | 6.68% N |

EXAMPLE 10

6-O-Demethyl-6-O-(phenylmethylaminocarbonyl) galanthamine Monohydrate Hydrochloride To a mixture of 0.80 g of 6-O-demethylgalanthamine and 0.82 g of milled potassium carbonate was added 13.5 ml of dry THF. The suspension was cooled to 0° C. after which was added 0.45 ml of benzyl isocyanate. The suspension was stirred at 0° C. for ½ hour and filtered onto a flash chromatography column, packed with silica gel, eluted with 3% dry methyl alcohol:chloroform followed by 5% dry methyl alcohol:chloroform. The product-containing fractions were combined and concentrated to provide 0.96 g of a white, amorphous solid. The solid was dissolved in chloroform, diluted with ethyl ether and the hydrochloride salt precipitated by addition of ethereal hydrogen chloride to provide 0.78 g of 6-demethyl-6-O-(phenylmethylaminocarbonyl) galanthamine monohydrate hydrochloride. Trituration/ recrystallization using isopropyl alcohol provided 0.52 g, m.p. 210–212° C.

| ANALYSIS | | | |
|---|---|---|---|
| Calculated for $C_{24}H_{28}N_2O_5 \cdot HCl$ | 62.54% C | 6.34% H | 6.08% N |
| Found | 62.89% C | 6.28% H | 6.07% N |

EXAMPLE 11

6-O-Demethyl-6-O-(n-nonylaminocarbonyl) galanthamine Hydrochloride

To a mixture of 0.80 g of 6-O-demethylgalanthamine and 0.81 g of milled potassium carbonate was added 13.5 ml of dry THF. The suspension was cooled to 0° C. after which was added 0.69 ml of n-nonyl isocyante. The suspension was stirred at 0° C. for ½ hour and at room temperature for 45 minutes. The suspension was filtered onto a flash chromatography column packed with silica gel, and eluted with 3% dry methyl alcoholchloroiorm followed by 5% dry methyl alcohol.chloroform. The product-containing fractions were combined and concentrated to provide 1.23 g of a yellow oil.

The oil was dissolved in ethyl ether and the hydrochloride salt precipitated by addition of ethereal hydrogen chloride to provide 1.07 g of 6-O-demethyl-6-O-(n-nonylaminocarbonyl)galanthamine hydrochloride. Trituration/recrystallization of the desired product using isopropyl alcohol provided 0.90 g, m.p. 205–208° C.

| ANALYSIS | | | |
|---|---|---|---|
| Calculated for $C_{26}H_{38}N_2O_4 \cdot HCl$ | 65.19% C | 8.21% H | 5.85% N |
| Found | 65.26% C | 8.34% H | 5.73% N |

EXAMPLE 12

6-O-Demethyl-3-O,6-O-bis(n-butylaminocarbonyl) galanthamine Hydrochloride

To a stirred suspension of 1.0 g of 6-O-demethylgalanthamine, and 17.5 ml of dry THF was added 1.5 ml of n-butyl isocyanate. The mixture in a sealed tube was stirred at 67° for 72 hours. The solution was concentrated to an oil and flash chromatographed on silica gel, eluting with 5% methanol/chloroform. The pure product-containing fractions were combined and concentrated to provide a quantitative yield of the bis carbamate as a yellow oil. The hydrochloride salt was precipitated by addition of ethereal hydrogen chloride and the salt isolated by filtration to provide a white solid which was dried for 2 hours at 80°. The yield of 6-O-demethyl-3-O,6-O-bis(n-butylaminocarbonyl)galanthamine hydrochloride was 0.692 g, m.p. 208–210° C.

| ANALYSIS | | | |
|---|---|---|---|
| Calculated for $C_{26}H_{37}N_3O_5 \cdot HCl$ | 61.47% C | 7.54% H | 8.27% N |
| Found | 61.15% C | 7.75% H | 8.19% N |

EXAMPLE 13

6-O-Demethy-6-O-(methylaminocarbonyl)-3-O-(propan-2-yl-carbonyl)galanthamine Hydrochloride To a cold suspension of 6-O-demethyl-6-O-(methylaminocarbonyl)galanthamine (EXAMPLE 2) (2.3 g) in 120 ml of dichloromethane, was added 4-dimethylaminopyridine (1.4 g) followed by a solution of isobutyric anhydride (1.5 ml) in 10 ml of dichloromethane. After stirring at ambient temperature for seven hours, the mixture was added directly to a silica gel column and eluted with 5% methanol/dichloromethane via HPLC. The desired fractions were combined and evaporated to a thick yellow oil, (2.0 g) which was dissolved in ether and adjusted to pH 1 with ethereal-HCl. The resultant white precipitate was collected and dried to give 1.7 g 135° C. (dec.)

| ANALYSIS | | | |
|---|---|---|---|
| Calculated for $C_{22}H_{28}N_2O_5 \cdot HCl$ | 60.47% C | 6.69% H | 6.41% N |
| Found | 59.95% C | 6.27% H | 6.26% N |

EXAMPLE 14

6-O-Demethyl-6-O-(n-octylaminocarbonyl)-3-O-(propan-2-yl-carbonyl)galantamine Hydrochloride To a stirred suspension of 0.82 g of 6-O-demethyl-6-O-(n-octylamino-carbonyl)galanthamine (EXAMPLE 9) in 20.5 ml of dichloromethane was added 0.42 g of DMAP, dissolved in 1 ml of dichloromethane. The suspension was cooled to 0° C. after which 0.41 ml of isobutyric anhydride was added. After a few minutes at 0° C., the reaction mixture was allowed to proceed at room temperature overnight. The mixture was then filtered onto a flash chromatography column, packed with silica gel and 3% dry methanol:chloroform, and eluted with the same solvent system followed by 5% dry methanol:chlorofonn. The product-containing fractions were combined and concentrated to provide 1.09 g of an oil. Precipitation of the hydrochloride salt using ethereal hydrogen chloride provided 0.65 g of 6-O-demethyl6-O-(n-octylamino-carbonyl)-3-O-(propan-2-yl-carbonyl)galanthamine hydrochloride, m.p. 137–140° C.

| ANALYSIS | | | |
|---|---|---|---|
| Calculated for $C_{29}H_{42}N_2O_5 \cdot HCl$ | 65.09% C | 8.10% H | 5.23% N |
| Found | 65.15% C | 8.27% H | 5.08% N |

EXAMPLE 15

6-O-Demethyl-6-O-(n-octylaminocarbonyl)-3-O-(t-butylcarbonyl)galanthamine Monohydrate Hydrochloride To 0.95 g of 6-O-demethyl6-O-(n-octylaminocarbonyl) galanthamine (EXAMPLE 9) was added 10 ml of dichloromethane via a syringe. The solution was stirred for a few minutes at room temperature after which was added 0.40 ml of triethylamine followed by 0.29 ml of trimethylacetyl chloride and 0.06 g of DMAP dissolved in 2 ml of dichloromethane. After stirring at room temperature for 4½ hours, the suspension was filtered onto a flash chromatography column, packed with silica gel and 3% methyl alcohol:chloroform and eluted with the same solvent followed by 5% methyl alcohol:chloroforn. The productontaining fractions were combined and concentrated to provide 1.12 g of a yellow oil. The oil was dissolved in diethyl ether and the hydrochloride salt precipitated by addition of ethereal hydrogen chloride to provide 0.93 g of 6-O-demethyl-6-O-(n-octylaminocarbonyl)-3-(trimethylacetylcarbonyl) galanthamine monohydrate hydrochloride, m.p. 138–140° C.

| ANALYSIS | | | |
|---|---|---|---|
| Calculated for $C_{30}H_{46}N_2O_6 \cdot HCl$ | 63.53% C | 8.35% H | 4.94% N |
| Found | 63.66% C | 8.00% H | 5.35% N |

EXAMPLE 16

7-Bromo-6-O-demethylgalanthamine

To a stirred solution of 1.38 ml (0.966 g) of t-butylamine in 36 ml of azeotripically dried toluene at −20 to −30° C. was added dropwise 0.34 ml (1.05 g) of bromine such that the temperature remained between −20 to −30° C. The solution was then cooled to −70 to −75° C. and a solution of 3.0 g of 6-O-demethylgalanthamine in 15 ml of DMF was added slowly by syringe such that the temperature did not rise above −70° C. The solution was stirred for 2 hours at −70 to −78° C. and subsequently allowed to warm slowly to room temperature over 6 hours. The solution was again cooled to 0° C., poured into ice/NaHCO$_3$/water, and extracted with chloroform. The aqueous fraction was saturated with NaCl and extracted 3 times with chloroform. The chloroform extracts were dried (Na$_2$SO$_4$), filtered and concentrated to an oil which was purified by HPLC, employing a Waters Prep 500 Instrument, and eluting with 30% methanol/chloroform, followed by 5% methanol/chloroform. The pure product-containing fractions were combined and concentrated to provide 1.83 g (47.3% based on 6-O-demethylgalanthamine, 78.9% based on bromine, the limiting reagent). Crystallization from acetone provided analytically pure 7-bromo-6-O-demethylgalanthamine, m.p. 138–141° C.

| ANALYSIS | | | |
|---|---|---|---|
| Calculated for $C_{16}H_{18}BrNO_3$ | 54.56% C | 5.15% H | 3.58% N |
| Found | 54.62% C | 5.50% H | 3.61% N |

EXAMPLE 17

6-O-Demethyl-6-O-(n-pentadecylaminocarbonyl) galanthamine Hydrochloride

To a stirred suspension of 0.80 g of demethylgalanthamine in 10 ml of dry dichloromethane was added 0.50 g of carbonyldiimidazole. The mixture was stirred at room temperature for 1 hour and cooled in an ice bath after which was added 0.57 ml of acetic acid and 0.79 g of pentadecylamine. The reaction mixturewas stirred at room temperature for 4.5 hours, poured into a cold saturated solution of NaHCO3, and extracted with chloroform. The organic layer was washed with water, dried over Na$_2$SO$_4$, filtered, and concentrated to a yellow oil. The oil was dissolved in chloroform and pipetted onto a flash chromatography column packed with silica gel and 3% methanol:chloroform The column was eluted with the same solvent system followed by 5% methanol:chloroform. The pure, product-containing fractions were combined and concentrated to a yellow oil weighing 0.72 g. The oil was dissolved in diethyl ether and the hydrochloride salt precipitated by addition of etheral hydrogen chloride to provide 6-O-demethyl-6-O-(n-pentadecylaminocarbonyl)galanthamine hydrochloride, m.p. 188–191° C. d.

| ANALYSIS: | | | |
|---|---|---|---|
| Calculated for $C_{32}H_{50}N_2O_4 \cdot HCl$: | 68.24% C | 9.13% H | 4.97% N |
| Found: | 67.91% C | 9.08% H | 5.08% N |

EXAMPLE 18

6-O-Demethyl-6-O-(dimethylaminocarbonyl) galanthamine Hydrochloride

To a stirred suspension of 0.81 g of 6-O-(demethylgalanthamine, 8.1 ml of dry chloroform, and 0.29 ml of dimethylcarbamyl chloride was added 0.44 ml of 1,8-diazabicyclo[5.4.0]-undec-7-ene. The mixture was allowed to stir at room temperature overnight after which it was filtered onto a flih chromatography column, packed with silica gel and 3% tethanol:chloroform and eluted with the same solvent system, followed by 5% nwthanolchlorofom The pure, product containing fractions were combined and concentrated to provide 0.56 g of an offwhite solid. Recrystalztion of the solid using cyclohexane:ether, followed by precipitation of the hydrochloride salt using ethereal hydrogen chloride provided 6-O-demethyl-6-O-(dimethylaminocarbonyl)-galanthamine hydrochloride, m.p. 270–272° C.d.

| ANALYSIS: | | | |
|---|---|---|---|
| Calculated for $C_{19}H_{24}N_2O_4 \cdot HCl$: | 59.92% C | 6.62% H | 7.36% N |
| Found: | 59.72% C | 6.61% H | 7.23% N |

It should be understood that this specification and examples are set forth by way of illustration and not limitation and that various modifications and changes may be made without departing from the spirit and scope of the present invention as defined by the appended claims.

What is claimed is:

1. A compound of the formula

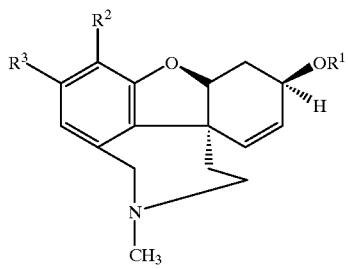

(II)

wherein
$R^1$ is selected from the group consisting of hydrogen, $(C_1-C_{12})$alkylcarbonyl, $(C_1-C_{12})$alkoxycarbonyl, mono$(C_1-C_{12})$alkylaminocarbonyl and di$(C_1-C_{12})$alkylaminocarbonyl;
$R^2$ is selected from the group consisting of butylaminocarbonyloxy, isopropylaminocarbonyloxy, t-butylaminocarbonyloxy, n-pentylaminocarbonyloxy, n-hexylaminocarbonyloxy, n-heptylaminocarbonyloxy, n-octylaminocarbonyloxy, n-nonylaminocarbonyloxy, and aryl$(C_1-C_4)$alkylaminocarbonyloxy; and
$R^3$ is hydrogen or bromine; or a pharmaceutically acceptable acid addition thereof, provided $R^1$ is not hydrogen when $R^2$ is methylaminocarbonyloxy.

2. The compound of claim 1 wherein
$R^1$ is selected from the group consisting of hydrogen, $(C_1-C_{10})$alkylcarbonyl, $(C_1-C_{10})$alkoxycarbonyl, mono$(C_1-C_{12})$alkylaminocarbonyl and di$(C_1-C_8)$alkylaminocarbonyl; and
$R^2$ is selected from the group consisting of butylaminocarbonyloxy, isopropylaminocarbonyloxy, t-butylaminocarbonyloxy, n-pentylaminocarbonyloxy, n-hexylaminocarbonyloxy, n-heptylaminocarbonyloxy, n-octylaminocarbonyloxy, n-nonylaminocarbonyloxy, and phenyl$(C_1-C_3)$alkylaminocarbonyloxy, or a pharmaceutically acceptable acid addition thereof, provided $R^1$ is not hydrogen when $R^2$ is methylaminocarbonyloxy.

3. The compound of claim 2 wherein
$R^1$ is selected from the group consisting of hydrogen, $(C_1-C_8)$alkylcarbonyl and $(C_1-C_8)$alkoxycarbonyl;
$R^2$ is selected from the group consisting of butylaminocarbonyloxy, isopropylaminocarbonyloxy, t-butylaminocarbonyloxy, n-pentylaminocarbonyloxy, n-hexylaminocarbonyloxy, n-heptylaminocarbonyloxy, n-octylaminocarbonyloxy and n-nonylaminocarbonyloxy; and
$R^3$ is hydrogen; or a pharmaceutically acceptable acid addition salt thereof, provided $R^1$ is not hydrogen when $R^2$ is methylaminocarbonyloxy.

4. The compound of claim 3 wherein $R^1$ is selected from the group consisting of hydrogen, methylcarbonyl, ethylcarbonyl, isopropylcarbonyl, t-butylcarbonyl, n-heptylcarbonyl and t-butoxycarbonyl, or a pharmaceutically acceptable acid addition thereof.

5. A method of treating memory dysfunction characterized by decreased cholinergic function which compises administering to a mammal an acetylcholinesterase inhibiting amount of the compound of claim 1.

6. The compound of claim 3 which is 6-O-demethyl-6-O-(n-heptylaminocarbonyl)galanthamine or a pharmaceutically acceptable acid addition salt thereof.

7. The compound of claim 3 which is 6-O-demethyl-6-O-(n-butylaminocarbonyl)galanthamine or a pharmaceutically acceptable acid addition salt thereof.

8. The compound of claim 3 which is 6-O-demethyl-6-O-(n-hexylaminocarbonyl)galanthamine or a pharmaceutically acceptable acid addition sal thereof.

9. The compound of claim 3 which is 3-O-acetyl-6-O-demethyl- 6-O-(methylaminocarbonyl)galanthamine or a pharmaceutically acceptable acid addition salt thereof.

10. The compound of claim 3 which is 6-O-demethyl-6-O-(n-octylaminocarbonyl)galanthamine or a pharmaceutically acceptable acid addition salt thereof.

11. The compound of claim 2 which is 6-O-demethyl-3-O-bis(n-heptylaminocarbonyl)galanthamine or a pharmaceutically acceptable acid addition salt thereof.

12. The compound of claim 3 which is 6-O-demethyl-6-O-(t-butylaminocarbonyl)galanthamine or a pharmaceutically acceptable acid addition salt thereof.

13. The compound of claim 3 which is 6-O-demethyl-6-O-(phenylmethylaminocarbonyl)galanthamine or a pharmaceutically acceptable acid addition salt thereof.

14. The compound of claim 3 which is 6-O-demethyl-6-O-(n-nonylaminocarbonyl)galanthamine or a pharmaceutically acceptable acid addition salt thereof.

15. The compound of claim 2 which is 6-O-demethyl-3-O,6-O-bis(n-butylaminocarbonyl)galanthamine or a pharmaceutically acceptable acid addition salt thereof.

16. The compound which is 6-O-demethyl- 6-O-(methylaminocarbonyl)-3-O-(propan-2-yl-carbonyl) galanthamine or a pharmaceutically acceptable acid addition salt thereof.

17. The compound of claim 3 which is 6-demethyl-6-O-(n-octylaminocarbonyl)-3-O-(propan-2-yl-carbonyl)-galanthamine or a pharmaceutically acceptable acid addition salt thereof.

18. The compound of claim 1 which is 6-O-demethyl-6-O-(n-pentadecylaminocarbonyl)galanthamine or a pharmaceutically acceptable acid addition salt thereof.

19. The compound of claim 3 which is 6-O-demethyl-6-O-(dimethylaminocarbonyl)galanthamine or a pharmaceutically acceptable acid addition salt thereof.

20. The compound of claim 3 which is 6-O-demethyl-3-O-(t-butylcarbonyl)-6-O-(n-octylaminocarbonyl) galanthamine or a pharmaceutically acceptable acid addition salt thereof.

21. A pharmaceutical composition which comprises a pharmaceutically acceptable carrier and an acetylcholinesterase inhibiting amount of the compound of claim 1.

* * * * *